US00PP34217P2

(12) United States Plant Patent
Michele

(10) Patent No.: US PP34,217 P2
(45) Date of Patent: May 10, 2022

(54) ***MYRTUS* PLANT NAMED 'FAZ-RED'**

(50) Latin Name: *Myrtus communis*
Varietal Denomination: FAZ-RED

(71) Applicant: Fazio Michele, Bitetto (IT)

(72) Inventor: Fazio Michele, Bitetto (IT)

(73) Assignee: Sapho

( * ) Notice: Subject to any disclaimer, the term of this patent is extended or adjusted under 35 U.S.C. 154(b) by 0 days.

(21) Appl. No.: 17/375,437

(22) Filed: Jul. 14, 2021

(51) Int. Cl.
*A01H 5/12* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 6/00
See application file for complete search history.

*Primary Examiner* — Anne Marie Grunberg
(74) *Attorney, Agent, or Firm* — Cassandra Bright

(57) ABSTRACT

A new and distinct variety of *Myrtus* plant named 'FAZ-RED' is disclosed, characterized by bright green, aromatic foliage, abundant flowering, and a round plant habit. Foliage also exhibits a strong red coloration during several months of the year. Plants are observed to tolerate a temperature range between −7° C. and 40° C. The new variety is a *Myrtus*, normally used for outdoor ornamental purposes.

3 Drawing Sheets

Latin name of the genus and species: *Myrtus communis*.
Variety denomination: 'FAZ-RED'.

BACKGROUND OF THE INVENTION

The new cultivar was discovered as a naturally occurring branch mutation on an unnamed, unpatented *Myrtus communis* plant at a commercial nursery in Bitetto, Italy.

The parent is an unnamed variety of *Myrtus communis*. *Myrtus* 'FAZ-RED' was found and selected as a potential new variety by the inventor at the same nursery in Bitetto, Italy, in July 2014.

Asexual reproduction of the new cultivar has been performed by vegetative cuttings. This was first performed at a commercial nursery in Bitetto, Italy, in 2014, and has shown that the unique features of this cultivar are stable and reproduced true to type in multiple successive generations.

SUMMARY OF THE INVENTION

The cultivar 'FAZ-RED' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FAZ-RED' These characteristics in combination distinguish 'FAZ-RED' as a new and distinct *Myrtus* cultivar:

1. Persistent bright green leaves.
2. Small leaves.
3. Dark, brilliant red apical vegetation, persisting from November to March.
4. Increased tolerance to cold and heat.
5. Observed increased resistance to disease.
6. Round plant habit.
7. Abundant flowering.
8. Aromatic leaves.

PARENT COMPARISON

Plants of the new cultivar 'FAZ-RED' are comparable to the unnamed parent variety of *Myrtus communis*. The two *Myrtus* varieties are similar in most horticultural characteristics; however, the new variety 'FAZ-RED' differs in the following:

1. Foliage of 'FAZ-RED' is a more brilliant green than the parent.
2. 'FAZ-RED' has a rounder growth habit than the parent.
3. Foliage of 'FAZ-RED' retains its foliage and green foliage color after flowering, while foliage of the seed parent is prone to yellowing and falling after flowering.
4. 'FAZ-RED' has a longer internode than the seed parent.

COMMERCIAL COMPARISON

Plants of the new cultivar 'FAZ-RED' are comparable to the unpatented commercial variety *Myrtus communis* 'Tarentina'. The two *Myrtus* varieties are similar in most horticultural characteristics; however, the new variety 'FAZ-RED' differs in the following:

1. The new variety has foliage colored red for several months of the year, this comparator has green foliage throughout the year.
2. The new variety has a smaller, rounder plant shape than this comparator.

Plants of the new cultivar 'FAZ-RED' are comparable to the unpatented commercial variety *Myrtus communis* 'Nana'. The two *Myrtus* varieties are similar in most horticultural characteristics; however, the new variety 'FAZ-RED' differs in the following:

1. The new variety has foliage colored red for several months of the year, this comparator has green foliage throughout the year.

2. The new variety tolerates lower temperatures than this comparator.

BRIEF DESCRIPTION OF THE PHOTOGRAPHS

The accompanying photograph in FIG. 1 illustrates plants of about 1 year old outdoors at during February.

Figure 1:
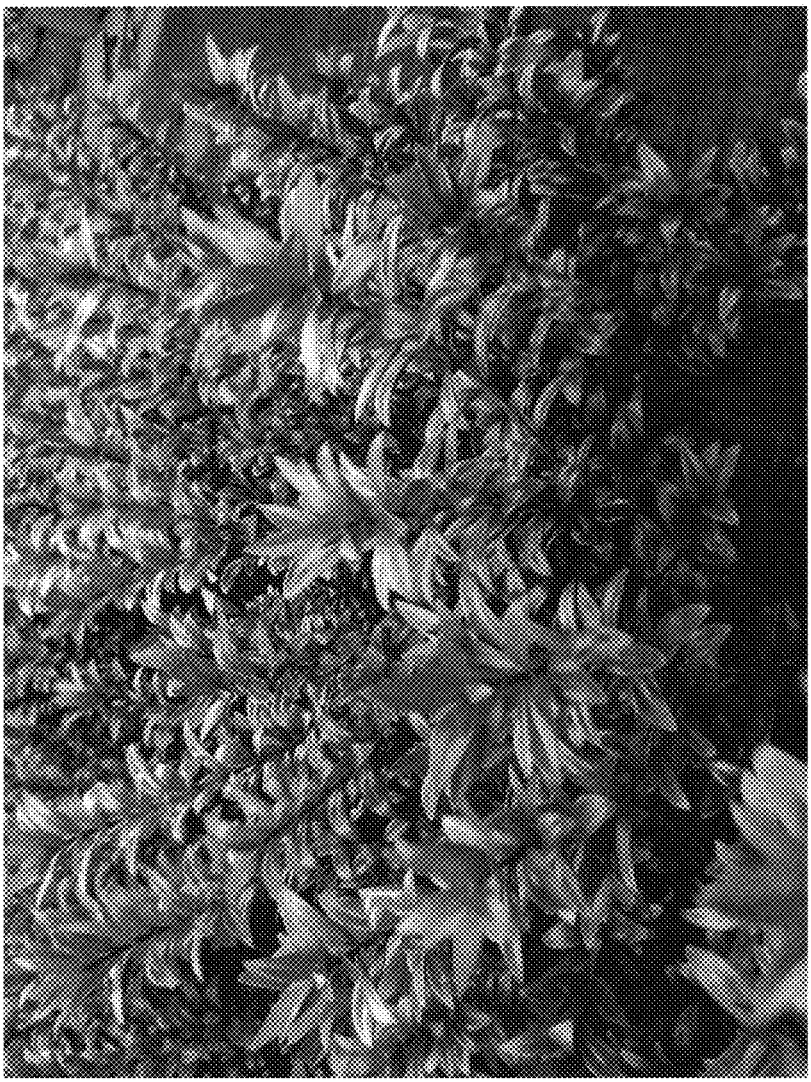
Figure 2:
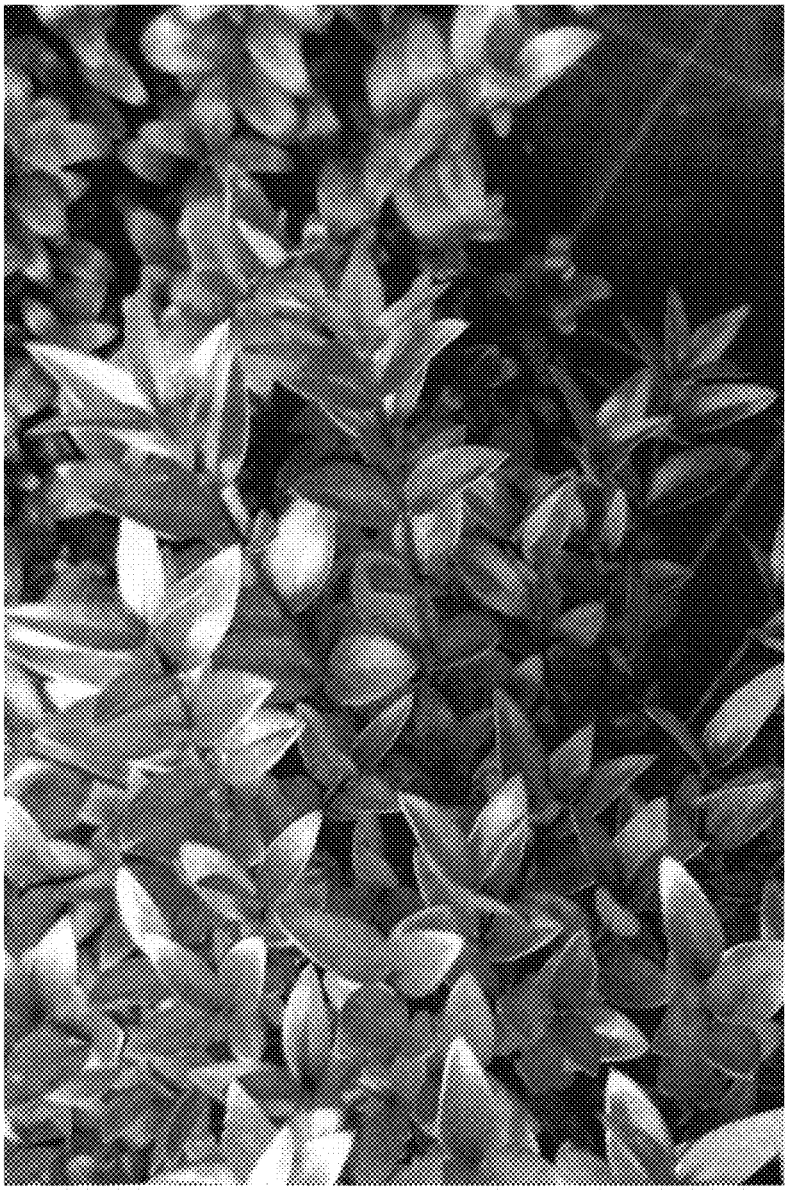
FIG. 2 illustrates a close-up of the foliage.
Figure 3:
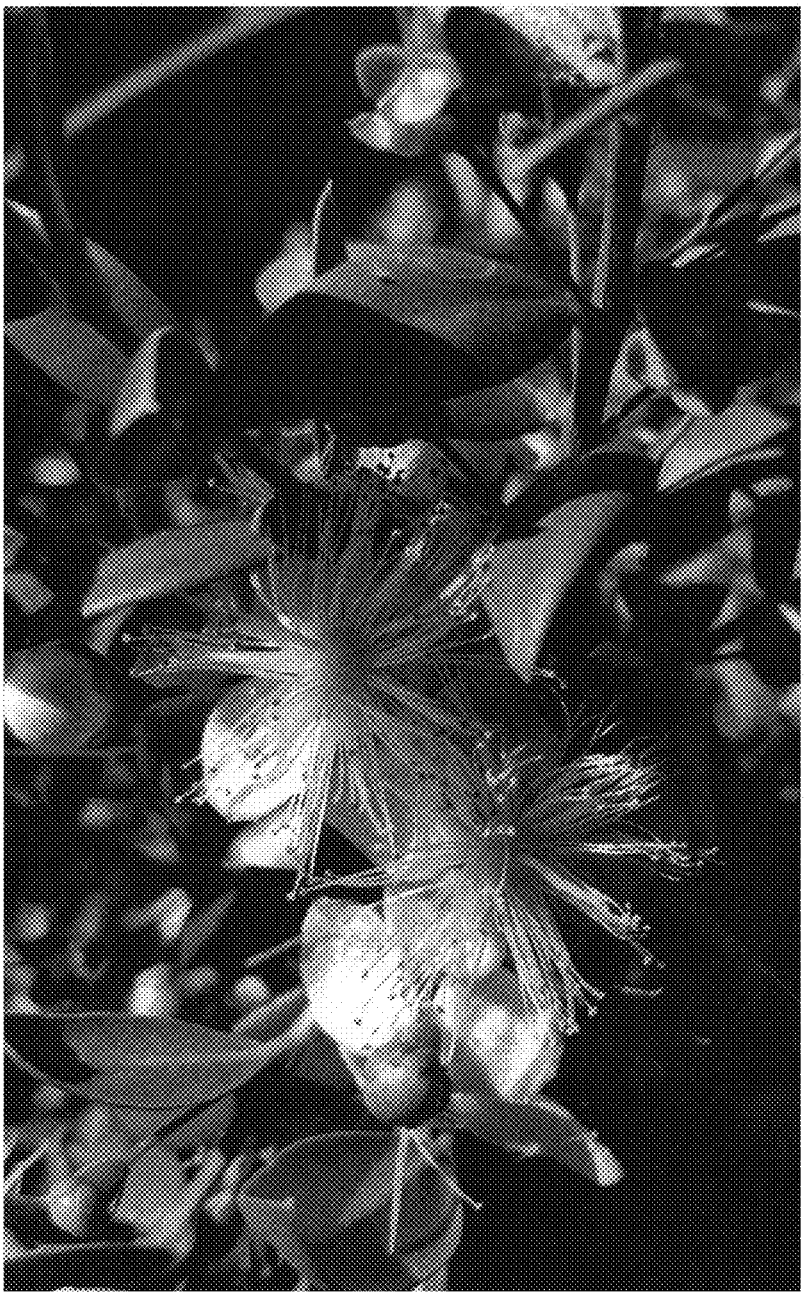
FIG. 3 illustrates a close-up view of typical flowers and buds of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'FAZ-RED' plants grown in a poly-house in Grand Haven, Mich. The growing temperature ranged from approximately 18° C. to 27° C. during the day and from approximately 5° C. to 10° C. during the night. General light conditions are normal sunlight and numerical values represent averages of typical plant types.

Botanical classification: *Myrtus communis* 'FAZ-RED'.

PROPAGATION

Type of propagation typically used: Vegetative terminal cuttings.

PLANT

Age of plant described: About 1 year.
Growth habit: Round.
Growth rate: Moderate.
Plant spread: 35 cm.
Plant height: 40 cm.
Mature size: 120 cm to 150 cm in height at five years of age.
Branching characteristics: Free, dense branching occurring at mainly acute angles.
Length of lateral branches: Average range 15 to 25 cm.
Diameter of lateral branches: Approximately 3 mm.
Quantity of lateral branches: 20 to 30.
Texture of lateral branches: Glabrous. Infrequent ridges.
Lateral branch shape: Round.
Lateral branch strength: Moderate, flexible.
Lateral branch color: Older/lower section near RHS Greyed-Orange, 164B flushed Greyed-Orange 165A. New growth near Greyed-Purple 187A.
Internode length: Average range 2.1 to 2.5 cm.

FOLIAGE

Leaf:
- *Arrangement.*—Opposite, single.
- *Average length.*—3 to 3.6 cm.
- *Average width.*—1.5 cm.
- *Shape of blade.*—Elliptic.
- *Apex.*—Acute.
- *Base.*—Tapered.
- *Margin.*—Entire.
- *Texture of top surface.*—Glabrous.
- *Texture of bottom surface.*—Glabrous.
- *Color.*—Young foliage upper side: Near RHS Green 137A. Young foliage under side: Near RHS Green 137C. Mature foliage upper side: RHS Green 139A. Mature foliage under side: RHS Green 137B. Red/bronze foliage upperside: Near RHS Greyed-Red 181A. Red/bronze foliage underside: Near RHS Greyed-Red 180B.
- *Venation.*—Type: Palmate. Venation color upper side: Mid-vein near RHS Yellow-Green 146D. Lateral veins indistinguishable from leaf blade. Venation color under side: RHS Yellow-Green 146D.
- *Durability of foliage to stress.*—Foliage is flexible, resisting breakage.
- *Fragrance.*—Moderately aromatic when crushed.

Petiole:
- *Length.*—Approximately 1 to 2 mm.
- *Diameter.*—Approximately 1 mm.
- *Color.*—Near RHS Yellow-Green 146D.
- *Texture.*—Glabrous.

FLOWER

Natural flowering season: Flowering begins in early June and continues until around mid-July in Southern California.

Flowers: Solitary, rotate with protruding stamens.
- *Diameter.*—1.5 to 2 cm.
- *Depth.*—About 1.0 excluding stamens. Stamens included about 2.1 cm.
- *Aspect.*—Upwardly facing.
- *Persistence.*—Slight persistence, then self cleaning.
- *Fragrance.*—Moderately aromatic.

Petals:
- *Arrangement.*—Whorled.
- *Number.*—5 to 10.
- *Shape.*—Obovate.
- *Margin.*—Entire.
- *Tip shape.*—Acute.
- *Base shape.*—Tapered.
- *Length.*—About 1 cm.
- *Width.*—About 7 mm.
- *Texture.*—Upper: Glabrous. Lower: Glabrous.
- *Color.*—When opening: Upper surface: Near RHS White 155A. Under surface: Near RHS White 155A. Fully opened: Upper surface: Near RHS White 155A. Under surface: Near RHS White 155A.

Bud:
- *Shape.*—Globular.
- *Length.*—About 7 mm.
- *Diameter.*—About 7 mm.
- *Color.*—Near RHS White 155A flushed greyed-Red 180C at base.

Sepals:
- *Arrangement.*—Rotate.
- *Number.*—5.
- *Shape.*—Deltoid.
- *Margin.*—Entire.
- *Tip shape.*—Acute.
- *Base shape.*—Truncate.
- *Length.*—About 4 mm.
- *Width.*—About 3 mm.
- *Texture.*—Upper: Glabrous. Lower: Glabrous.
- *Color.*—Upper surface: Near RHS Green 138A. Under surface: Near RHS Green 138B.

Peduncle:
*Length.*—About 2 to 3 cm.
*Diameter.*—About 2 mm.
*Texture.*—Glabrous.
*Color.*—Near RHS Green 138A.
*Strength.*—Moderately strong.

REPRODUCTIVE ORGANS

Stamens:
*Number.*—About 40 to 60.
*Filament length.*—About 1.8 cm.
*Filament color.*—Near White 155A.
Anthers:
*Shape.*—Globular.
*Diameter.*—2 mm.
*Color.*—Near Yellow 12D.
*Pollen.*—Amount: Scant. Color: Near Yellow 12D.
Pistil:
*Number.*—1.
*Length.*—About 1.7 cm.
*Style.*—Length: About 1.5 cm. Color: Near White 155A.
Stigma:
*Shape.*—Linear.
*Color.*—Near White 155A.

OTHER CHARACTERISTICS

Fruits and seeds: Not observed to date.
Disease resistance: Resistance to typical diseases of *Myrtus communis* observed. The exact diseases are unconfirmed, however, typical diseases of *Myrtus communis* include *Phytoplasmas asteris* and *Pseudomonas savastanoi*.
Temperature range: Observed to tolerate low temperature of −7° C. and a high temperature of 40° C.

What is claimed is:
1. A new and distinct cultivar of *Myrtus* plant named 'FAZ-RED' as herein illustrated and described.

* * * * *